(12) United States Patent
Marg et al.

(10) Patent No.: US 11,414,647 B2
(45) Date of Patent: Aug. 16, 2022

(54) METHOD FOR CULTIVATING STEM CELLS IN VITRO

(71) Applicant: Simone Spuler, Berlin (DE)

(72) Inventors: Andreas Marg, Berlin (DE); Simone Spuler, Berlin (DE)

(73) Assignee: Simone Spuler, Berlin (DE)

( * ) Notice: Subject to any disclaimer, the term of this patent is extended or adjusted under 35 U.S.C. 154(b) by 328 days.

(21) Appl. No.: 15/506,726

(22) PCT Filed: Aug. 25, 2015

(86) PCT No.: PCT/EP2015/069442
§ 371 (c)(1),
(2) Date: Feb. 24, 2017

(87) PCT Pub. No.: WO2016/030371
PCT Pub. Date: Mar. 3, 2016

(65) Prior Publication Data
US 2017/0275590 A1 Sep. 28, 2017

(30) Foreign Application Priority Data
Aug. 25, 2014 (DE) ...................... 10 2014 216 872.4

(51) Int. Cl.
*C12N 5/077* (2010.01)
*A61K 35/34* (2015.01)

(52) U.S. Cl.
CPC ............ *C12N 5/0659* (2013.01); *A61K 35/34* (2013.01); *C12N 2500/02* (2013.01); *C12N 2523/00* (2013.01)

(58) Field of Classification Search
CPC .......................... C12N 5/0659; C12N 2523/00
See application file for complete search history.

(56) References Cited

U.S. PATENT DOCUMENTS

| | | | |
|---|---|---|---|
| 6,184,035 B1 * | 2/2001 | Csete ................. | A61K 38/1816 435/375 |
| 2008/0152627 A1 * | 6/2008 | Chancellor ............ | A61K 35/34 424/93.7 |
| 2012/0244067 A1 * | 9/2012 | Roth ........................ | A01N 1/02 424/1.11 |

FOREIGN PATENT DOCUMENTS

| WO | 2009/121002 A1 | 10/2009 | |
| WO | WO-2010050073 A1 * | 5/2010 | ........... A01N 1/0263 |
| WO | 2013/025766 A1 | 2/2013 | |
| WO | 2014/039654 A1 | 3/2014 | |

OTHER PUBLICATIONS

Jeanne et al., "Low oxygen and high-carbon-dioxide atmosphere improves the conservation of hematopoietic progenitors in hypothermia", Transplantation and Cellular Engineering, Transfusion, 2009, vol. 49, pp. 1738-1746. (Year: 2009).*
Bolognesi et al., "Protective Effect of Hypothermia on Contractile Force in Skeletal Muscle", Journal of Orthopaedic Research, 1996, vol. 14, No. 3, pp. 390-395. (Year: 1996).*
Collins et al., "Self-Renewal of the Adult Skeletal Muscle Satellite Cell", Cell Cycle, 2005, vol. 4, No. 10, pp. 1338-1341. (Year: 2005).*
Langenbach, F. et al., "Osteogenic Differentiation Influences Stem Cell Migration Out of Scaffold-Free Microspheres", Tissue Engineering Part A, vol. 16, No. 2, Feb. 1, 2010 (Feb. 1, 2010), pp. 759-766.
Parker, M.H. et al., "Activation of Notch Signaling During Ex Vivo Expansion Maintains Donor Muscle Cell Engraftment", Stem Cells, vol. 30, No. 10,Sep. 20, 2012 (Sep. 20, 2012), pp. 2212-2220.
European Examination Report issued in corresponding application No. 15763506.1, dated Sep. 3, 2019.
Ammar et al., "The Sleeping Beauty transposon toolbox", Methods in Molecular Biology, vol. 859, Jan. 31, 2012, pp. 229-240.
Bröhl et al., "Colonization of the Satellite Cell Niche by Skeletal Muscle Progenitor Cells Depends on Notch Signals", Developmental Cell, Sep. 11, 2012, vol. 23, Issue 3, pp. 469-481.
Beauchamp et al., "Expression of CD34 and Myf5 Defines the Majority of Quiescent Adult Skeletal Muscle Satellite Dells", The Journal of Cell Biology, vol. 151, Issue 6, Dec. 11, 2000, pp. 1221-1233.
Blanco-Bose et al., "Purification of mouse primary myoblasts based on alpha 7 integrin expression", Experimental Cell Research, vol. 265, Issue 2, May 1, 2001, pp. 212-220.
Boldrin et al., "Donor satellite cell engraftment is significantly augmented when the host niche is preserved and endogenous satellite cells are incapacitated", Stem Cells, vol. 30, Issue 9, Sep. 2012, pp. 1971-1984.
Conboy, I.M. and Rando, T.A., "The Regulation of Notch Signaling Controls Satellite Cell Activation and Cell Fate Determination in Postnatal Myogenesis", Developmental Cell, vol. 3, Issue 3, Sep. 2002, pp. 397-409.
Cerletti et al., "Highly Efficient, Functional Engraftment of Skeletal Muscle Stem Cells in Dystrophic Muscles", Cell, vol. 134, Issue 1, Jul. 11, 2008, pp. 37-47.
Cornelison et al., "Syndecan-3 and syndecan-4 specifically mark skeletal muscle satellite cells and are implicated in satellite cell maintenance and muscle regeneration", Developmental Biology, vol. 239, Issue 1, Nov. 1, 2001, pp. 79-94.
Corwin et al., "Characterization and Modulation of Human Mesenchymal Stem Cell Stress Pathway Response Following Hypothermic Storage", Cryobiology, vol. 68, Issue 2, Apr. 2014, pp. 215-226.
Dellavalle et al., "Pericytes of human skeletal muscle are myogenic precursors distinct from satellite cells", Nature Cell Biology, vol. 9, Issue 3, Mar. 2007, pp. 255-267.

(Continued)

*Primary Examiner* — Laura Schuberg
(74) *Attorney, Agent, or Firm* — Acuity Law Group, PC; Michael A. Whittaker (57) ABSTRACT

The invention relates to method for cultivating stem cells in vitro, comprising the following steps: providing a sample comprising stem cells and cultivating the stem cells by subjecting the sample to a treatment for a first period of time. The treatment is carried out under hypothermic conditions having a defined temperature and a defined atmosphere, wherein the temperature does not exceed 15° C. and the atmosphere has an oxygen content not exceeding 21% (v/v). Thereby, the first period of time is 4 days to 4 weeks.

7 Claims, 1 Drawing Sheet

(56) References Cited

OTHER PUBLICATIONS

Filareto et al., "An ex vivo gene therapy approach to treat muscular dystrophy using inducible pluripotent stem cells", Nature Communications, vol. 4, Issue 1549, Mar. 5, 2013, pp. 1-9.

Gussoni et al., "Dystrophin expression in the mdx mouse restored by stem cell transplantation", Nature, vol. 401, Issue 5751, Sep. 23, 1999, pp. 390-394.

Gilbert et al., "Substrate elasticity regulates skeletal muscle stem cell selfrenewal in culture", Science, vol. 329, Issue 5995, Aug. 27, 2010, pp. 1078-1081.

Gustafsson et al., "Hypoxia Requires Notch Signaling to Maintain the Undifferentiated Cell State", Developmental Cell, vol. 9, Issue 5, Nov. 2005, pp. 617-628.

Irintchev et al., "Expression pattern of M-cadherin in normal, denervated, and regenerating mouse muscles", Developmental Dynamics, vol. 199, Issue 4, Apr. 1994, pp. 326-337.

Lepper et al., "An absolute requirement for Pax7-positive satellite cells in acute injury-induced skeletal muscle regeneration", Development, vol. 138, Issue 17, Sep. 2011, pp. 3639-3646.

Liu al., "Hypoxia Promotes Satellite Cell Self-Renewal and Enhances the Efficiency of Myoblast Transplantation", Development, vol. 139, Issue, 16, Aug. 15, 2012, pp. 2857-2865.

Latil et al., "Skeletal muscle stem cells adopt a dormant cell state post mortem and retain regenerative capacity", Nature Communications, vol. 3, Issue 903, Jun. 2012, pp. 1-12.

Mauro, "Satellite cell of skeletal muscle fibers", Journal of Biophysical & Biochemical Cytology, vol. 9, Issue 2, Feb. 1, 1961, pp. 493-495.

Mitchell et al., "Identification and characterization of a non-satellite cell muscle resident progenitor during postnatal development". Nature Cell Biology, vol. 12, Issue 3, Mar. 2010, pp. 257-266.

Mendell et al., "Myoblast transfer in the treatment of Duchenne's muscular dystrophy", The New England Journal of Medicine, vol. 333, Issue 13, Sep. 28, 1995, pp. 832-838.

Montarras et al., "Direct isolation of satellite cells for skeletal muscle regeneration", Science, vol. 309, Issue 5743, Sep. 23, 2005, pp. 2064-2067.

Mátés et al., "Molecular evolution of a novel hyperactive Sleeping Beauty transposase enables robust stable gene transfer in vertebrates", Nature Genetics, vol. 41, Issue 6, Jun. 2009, pp. 753-761.

Marg et al., "Human satellite cells have regenerative capacity and are genetically manipulable". The Journal of Clinical nvestigation, vol. 124, Issue 10, Aug. 26, 2014, pp. 4257-4265.

Oustanina et al., "Pax7 directs postnatal renewal and propagation of myogenic satellite cells but not their specification", The EMBO Journal, vol. 23, Issue 16, Aug. 18, 2004, pp. 3430-3439.

Partridge et al.,"Conversion of mdx myofibres from dystrophin-negative to -positive by injection of normal myoblasts", Nature, vol. 337, Issue 6203, 1989, pp. 176-179.

Relaix et al., "A Pax3/Pax7-dependent population of skeletal muscle progenitor cells", Nature, vol. 435, Issue 7044, Jun. 16, 2005, pp. 948-953.

Relaix et al., "Satellite cells are essential for skeletal muscle regeneration: the cell on the edge returns centre stage", Development, vol. 139, Issue 16, Aug. 2012, pp. 2845-2856.

Rocheteau et al., "A Subpopulation of Adult Skeletal Muscle Stem Cells Retains All Template DNA Strands after Cell Division", Cell, vol. 148, Issue 1-2, Jan. 20, 2012, pp. 112-125.

Sambasivan et al., "Pax7-expressing satellite cells are indispensable for adult skeletal muscle regeneration", Development, vol. 138, Issue 17, Sep. 2011, pp. 3647-3656.

Sampaolesi et al., "Cell therapy of alpha-sarcoglycan null dystrophic mice through intra-arterial delivery of mesoangioblasts", Science, vol. 301, Issue 5632, Jul. 25, 2003, pp. 487-492.

Seale et al., "Pax7 Is Required for the Specification of Myogenic Satellite Cells", Cell, vol. 102, Issue 6, Sep. 15, 2000, pp. 777-786.

Simon et al., "The role of oxygen availability in embryonic development and stem cell function", Nature Reviews Molecular Cell Biology, vol. 9, Issue 4, Apr. 2008, pp. 285-296.

Yin et al., "Satellite Cells and the Muscle Stem Cell Niche", Physiological Reviews, vol. 93, Issue 1, Jan. 1, 2013, pp. 23-67.

Vasyutina et al., "RBP-J (Rbpsuh) is essential to maintain muscle progenitor cells and to generate satellite cells", Proceedings of the National Academy of Sciences of The United States of America, vol. 104, Issue 11, Mar. 13, 2007, pp. 4443-4448.

Torrente et al., "Human circulating AC133+ stem cells restore dystrophin expression and ameliorate function in dystrophic skeletal muscle", The Journal of Clinical Investigation, vol. 114, Issue 2, Jul. 15, 2004, pp. 182-195.

Tedesco et al., "Repairing skeletal muscle: regenerative potential of skeletal muscle stem cells", The Journal of Clinical Investigation, vol. 120, Issue 1, Jan. 2010, pp. 11-19.

Bonavaud et al., "Preparation of isolated human muscle fibers: A Technical Report", In Vitro Cellular & Developmental Biology—Animal, vol. 38, No. 2, Feb. 2002, pp. 66-72.

Relaix et al., "Pax3 and Pax7 have distinct and overlapping functions in adult muscle progenitor cells", Journal of Cell Biology, vol. 172, Issue 1, Jan. 2, 2006, pp. 91-102.

JP Notification of Reasons for Rejection in application No. 2017-511293 dated Sep. 3, 2019.

Song, Y et al., Poultry Science, 89 (Feb. 2010), p. 123-124.

Van den Brink, et al. "Single-cell sequencing reveals dissociation-induced gene expression in tissue subpopulations" Nat Methods 14, 935-936 (2017). https://doi.org/10.1038/nmeth.4437.

Velleman et al. "Heterogeneity in growth and differentiation characteristics in male and female satellite cells isolated from turkey lines with different growth rates." Comparative Biochemistry and Physiology Part A: Molecular & Integrative Physiology 125 (2000): 503-509.

Supplement to Van De Brink et al., "Single-cell sequencing reveals dissociation-induced gene expression in tissue subpopulations", Nature Methods, Sep. 29, 2017;14(10):935 936. doi: 10.1038/nmeth. 4437, 65 pages.

Marg et al., "Human satellite cells have regenerative capacity and are genetically manipulable", J Clin Invest. 2014;124(10):4257-4265. https://do .org/10.1172/JCI63992.

* cited by examiner

METHOD FOR CULTIVATING STEM CELLS IN VITRO

CROSS-REFERENCE TO A RELATED APPLICATION

This application is a National Phase Patent Application of International Patent Application Number PCT/EP2015/069442, filed on Aug. 25, 2015, which claims priority of German Patent Application Number 10 2014 216 872.4, filed on Aug. 25, 2014.

BACKGROUND

The invention relates to a method for cultivating and enriching stem cells in vitro, to in vitro cultivated stem cells and to a method for generating genetic modified stem cells in vitro.

According to prior art, it is a challenge to cultivate stem cells in vitro such that they maintain alive but do not start to differentiate. Differentiation goes along with a loss of the omnipotent or pluripotent potential of stem cells.

It is also known from prior art that hypothermic treatment leads to stress for cells such that their viability significantly decreases. It was tried to reduce the stress by addition of certain compounds such as resveratrol (Corwin et al.: Characterization and modulation of human mesenchymal stem cell stress pathway response following hypothermic storage, Cryobiology 68 (2014), 215-226).

WO 2009/121002 A1 describes a method for hypothermic collecting of whole blood. It was shown that a preservation can be achieved by cooling blood over a time period of 1 to 3 days if a preservation solution is added.

Stem cells can be used for novel growth of tissue in vitro or in vivo.

SUMMARY

It is an object of the instant invention to provide a method for cultivating and enriching stem cells in vitro, wherein the stem cells retain their omnipotent or pluripotent potential.

This object is achieved with a method having features as described herein. Such a method for cultivating and enriching stem cells in vitro comprises the following steps: providing a sample comprising stem cells and cultivating the stem cells by subjecting the sample to a treatment for a first period of time. The method is characterized in that the treatment is carried out under hypothermic conditions having a defined temperature and a defined atmosphere, wherein the temperature does not exceed 15° C. and the atmosphere has an oxygen content not exceeding 21 volume % (in the following indicated as % (v/v)). Thereby, the first period of time is 4 days to 4 weeks. The cultivation under these conditions surprisingly leads to an enrichment of stem cells in the sample such that approximately 70 to 100% of all viable cells in the sample are cultivated stem or derivatives from cultivated stem cells after the first period of time.

Prior art does not suggest at all that such an enrichment could be possible, i.e. that stem cells can be selectively cultivated and thus enriched in a cell culture by the treatment conditions according to the claimed invention. One would have rather suspected that stem cells do not well tolerate low temperatures but that low temperatures are stress for stem cells, too. Furthermore, it was very surprising that a significant enrichment does not occur at incubation periods of shorter than 4 days.

The cultivation takes place by using a medium that is suited or adapted for the stem cells to be cultivated.

In an embodiment, the temperature does not exceed 14° C., in particular 13° C., in particular 12° C., in particular 11° C., in particular 10° C., in particular 9° C., in particular 8° C., in particular 7° C., in particular 6° C., in particular 5° C., in particular 4° C., in particular 3° C., in particular 2° C. in particular 1° C., in particular 0° C. In an embodiment, the temperature is in a range of 0° C. to 15° C., in particular 1° C. to 14° C., in particular 2° C. to 13° C., in particular 3° C. to 12° C., in particular 4° C. to 11° C., in particular 5° C. to 10° C., in particular 6° C. to 9° C., in particular 7° C. to 8° C.

In an embodiment, the atmosphere has an oxygen content not exceeding 20 volume %, in particular 19% (v/v), in particular 18% (v/v), in particular 17% (v/v), in particular 16% (v/v), in particular 15% (v/v), in particular 14% (v/v), in particular 13% (v/v), in particular 12% (v/v), in particular 11% (v/v), in particular 10% (v/v), in particular 9% (v/v), in particular 8% (v/v), in particular 7% (v/v), in particular 6% (v/v), in particular 5% (v/v), in particular 4% (v/v), in particular 3% (v/v), in particular 2% (v/v), in particular 1% (v/v), in particular not exceeding any of the before-mentioned oxygen contents.

Conditions having an atmosphere with an oxygen content of less than 20% (v/v) are often also referred to as hypoxic conditions.

In an embodiment, the atmosphere has an oxygen content lying in a range of 1% (v/v) to 21% (v/v), in particular of 2% (v/v) to 20% (v/v), in particular of 3% (v/v) to 19% (v/v), in particular of 4% (v/v) to 18% (v/v), in particular of 5% (v/v) to 17% (v/v), in particular of 6% (v/v) to 16% (v/v), in particular of 7% (v/v) to 15% (v/v), in particular of 8% (v/v) to 14% (v/v), in particular of 9% (v/v) to 13% (v/v), in particular of 10% (v/v) to 12% (v/v), in particular of 3% (v/v) to 11% (v/v).

Any combinations of the above-given temperature and oxygen contents are herewith explicitly disclosed.

In an alternative embodiment, the atmosphere has an oxygen content not exceeding 30 volume %, in particular not exceeding 29% (v/v), in particular not exceeding 28% (v/v), in particular not exceeding 27% (v/v), in particular not exceeding 26% (v/v), in particular not exceeding 25% (v/v), in particular not exceeding 24% (v/v), in particular not exceeding 23% (v/v), in particular not exceeding 22% (v/v), in particular not exceeding 21% (v/v), In an embodiment, the temperature is in a range of 0° C. to 10° C. and the oxygen content is in a range of 0% (v/v) to 8% (v/v). In an embodiment, the temperature is in a range of 2° C. to 5° C. and the oxygen content is in a range of 2% (v/v) to 5% (v/v). In an embodiment, the temperature is in a range of 3° C. to 4° C. and the oxygen content is in a range of 3% (v/v) to 4% (v/v).

If not explicitly stated otherwise, all percentages indicating a fluid content or fraction are expressed in % (v/v), even if the addition (v/v) is missing.

In an embodiment, the first period of time is 1 week to 4 weeks, in particular 2 weeks to 3 weeks.

It turned out that a duration of the first period of time of 5 days to 2 weeks, in particular of 6 days to 1 week, in particular 1 week is particularly suited for stem cell cultivation and enrichment.

In an embodiment, the stem cells are chosen from the group consisting of satellite cells, muscle stem cells (MuSCs), smooth muscle (SM) cell precursors, myoblasts, mesangioblasts, pericytes/myeloid-derived suppressor cells (MDSCs), side population stem cells (SP cells), CD133+ cells, induced pluripotent stem cells (IPS), mesenchymal stem cells (MSCs) and PW1-interstitial cells.

Satellite cells are particularly suited.

In an embodiment, the method does explicitly not make use of embryonic stem cells, in particular not of human embryonic stem cells.

In another embodiment, the stem cells are embryonic stem cells, provided that they have been obtained without destroying an embryo or a multi-cellular entity that is able to become an embryo.

In an embodiment, the stem cells are muscular satellite cells (Pax7$^+$ cells). Muscular satellite cells are necessary for muscle regeneration.

In an embodiment, the sample is an isolated tissue sample. It can be isolated from a subject by standard methods, such as a biopsy. A blood sample is also a suited tissue sample.

In an embodiment, the sample is an isolated muscle fiber fragment. Human muscle fiber fragments (HMFFs) are particularly suited and easily obtainable by a muscle biopsy.

In an embodiment, the stem cells are not cultivated in form of a cell suspension. I.e., in this embodiment, the cells are not cultivated in form of a classic cell culture in which cells are suspended in a medium without any supportive structure.

In an embodiment, the stem cells are cultivated in a united cell structure. This can best be achieved by a supportive structure that enables a united cell structure. In an embodiment, this supportive structure is the natural structure in which the cells grow in a body (such as a HMFF which is very well suited in the context of this invention to cultivate satellite cells). In another embodiment, this supportive structure is an artificial structure mimicking or closely resembling the natural structure in which the cells grow in a body.

In an embodiment, the sample is obtained from an organism belonging to the group consisting of mammals, homonidae, humans, non-human mammals and rodents. Humans are particularly suited.

In an embodiment, the temperature does not exceed 10° C. and the oxygen content does not exceed 8% (v/v).

In an embodiment, 70 to 100% (in particular 75 to 99%, in particular 80 to 95%, in particular 85 to 90%) of all viable cells in the sample are cultivated stem cells after the first period of time. To give an example, the percentage of Pax7$^+$ cells (true muscle stem cells, also referred to as satellite cells) among all myogenic cells (desmin$^+$) in culture varies around 40 to 50% without hypothermic treatment. However, in an experiment, the percentage rose up to 85% and remained that high after hypothermic treatment for several weeks.

In an embodiment, growth factors are added to the medium in which the stem cells are cultivated. In an embodiment, growth factors are only added if the stem cells are cultivated for more than 2 weeks, in particular for more than 2 weeks at 4° C. In particular in case of HMFF as sample and satellite cells to be cultivated, a medium with low serum content is suited. A well suited medium is a serum-reduced optimized minimal essential medium, such as OptiMEM, obtainable from Life Technologies.

In an embodiment, growth factors are not added to the medium in case of shorter periods of cultivation (in particular for a first period of time lying in the range of 4 to 14 days). For these shorter periods of cultivation, a glucose containing buffered salt solution can be well used as medium. A well suited medium is 30 mM HEPES, 130 mM NaCl, 3 mM KCl, 10 mM D-glucose, and 3.2 µM Phenol red (pH 7.6). Such a medium is in particular suited for cultivating muscle stem cells in clinical settings when xenogeneic serum should best be avoided during culture.

The invention also relates to cultivated stem cells, obtained by a method according to the previous explanations. Such cultivated stem cells generally show different molecular and metabolic characteristics than non-cultivated stem cells so that they can be distinguished from non-cultivated stem cells. They retain, however, their general characteristics regarding their omnipotent or pluripotent potential. As will be explained in more detail with respect to an exemplary embodiment, the cell colonies formed by hypothermically incubated stem cells differ from cell colonies of stem cells observed in vivo or under other incubation conditions regarding their structure and composition. To give an example, colonies of hypothermically treated satellite cells comprise up to 100% of myogenic cells. Thus, non-myogenic cells like fibroblasts do survive the hypothermic treatment.

Such a cell colony offers different growth properties in subsequent forms of usage than classic (non-hypothermically treated) cell colonies. The same holds true for human muscle fiber fragments that have been subjected to a hypothermic treatment.

In an aspect, the invention therefore also relates to a cell colony comprising cultivated stem cells that are obtainable by a method according to the preceding explanations. The invention further relates in an aspect to an isolated human muscle fiber fragment that is obtainable after carrying out a method according to the preceding explanations.

The invention also relates to a method for generating genetic modified stem cells in vitro, comprising the following steps: providing cultivated stem cells, obtained by a method according to any of the preceding explanations, and inserting genetic information into the cultivated stem cells.

In an aspect, the invention also relates to genetically modified stem cells that are obtainable by such a method for generating genetic modified stem cells in vitro.

In an aspect, the invention also relates to the medical use of cultivated stem cells or genetically modified stem cells. Thereby, the stem cells are intended to be used in treating a disorder by administering the cultivated stem cells or genetically modified stem cells to a subject in need thereof.

In an embodiment, the disorder is a muscular dystrophy such as, e.g., Duchenne's dystrophy or urinary bladder dystrophy. In an embodiment, the disorder is an amyotrophia, such as local or generalized amyotrophia.

Herewith, a method of transplanting cultivated stem cells to a subject in need thereof is disclosed, the method comprising administering stem cells cultivated as outlined above to the subject. The stem cell can originate from the treated subject (autologous transplantation) or from a different subject (allogeneic transplantation). The stem cell can be genetically modified, as explained directly above.

Herewith, a method of treating a subject suffering from a muscular dystrophy and/or an amyotrophia is disclosed, the method comprising administering muscular stem cells cultivated (and optionally genetically modified) as outlined above to the subject. In an embodiment, the muscular stem cells are satellite cells. In an embodiment, the stem cells are administered in form of a tissue system that has been treated as outlined in the claims for cultivating the stem cells, in particular in form of accordingly treated muscle fiber fragments, and very particular in form of a HMFF.

The embodiments described with respect to one of the disclosed methods can be applied to any of the other described or claimed methods and cells in an analogous way.

BRIEF DESCRIPTION OF THE DRAWING

Aspects of the invention will be explained in the following with respect to exemplary embodiments and a Figure.

DETAILED DESCRIPTION

Figure 1:
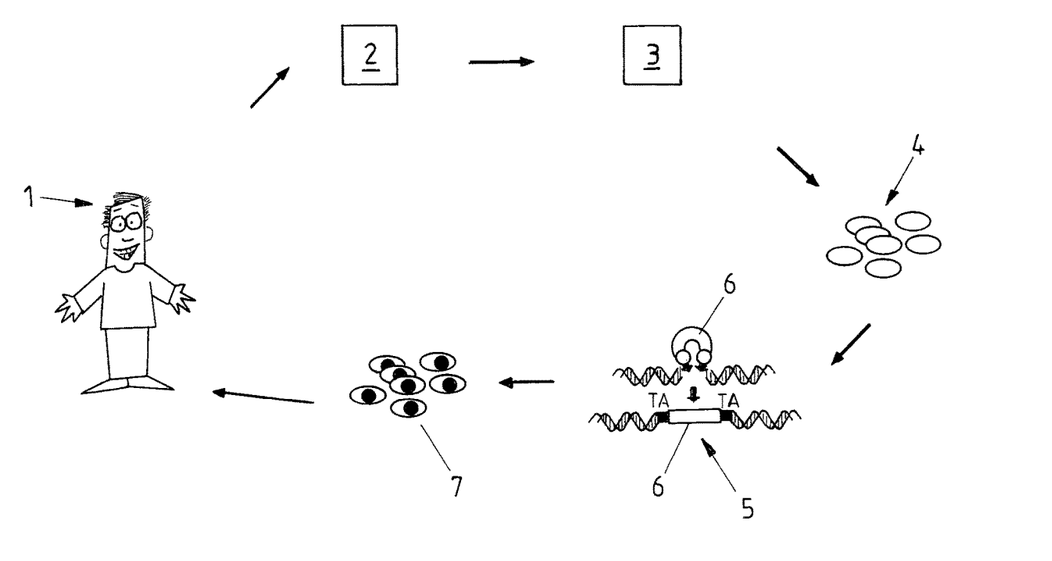
FIG. 1 shows a schematic depiction of a suited application of cultivated stem cells.

FIG. 1 shows a donor 1 from whom a muscle biopsy specimen 2 has been taken. This muscle biopsy specimen 2 is then transferred to a cell culture 3. By applying a cultivation method as hereinbefore described, an expansion of satellite cells 4 is achieved. The genetic code of these expanded satellite cells 4 is then modified in a gene repair step 5 by replacing defect genetic information with desired genetic information 6 or by introducing such desired genetic information 6 without replacing other genetic information.

Genetically corrected stem cells 7 result from the gene repair step 5. These genetically corrected stem cells 7 can then be administered (transplanted) to the donor 1 who thus acts also as acceptor.

Exemplary Embodiment: Human Satellite Cells Have Regenerative Capacity and Are Genetically Manipulable This exemplary embodiment has been published in the Journal of Clinical Investigation 124(10), published Aug. 26, 2014, pages 4257-4265 (hereinafter referred to as "the publication"). The publication including its supplemental material is hereby incorporated by reference in its entirety, in particular with respect to its Figures and the Figure legends. It forms part of the disclosure of the invention.

Summary

Muscle satellite cells promote regeneration and could improve gene delivery for treating muscular dystrophies. Human satellite cells are scarce; therefore, clinical investigation has been limited. The inventors obtained muscle fiber fragments from skeletal muscle biopsy specimens from adult donors aged 20 to 80 years. Fiber fragments were manually dissected, cultured, and evaluated for expression of myogenesis regulator PAX7. PAX7$^+$ satellite cells were activated and proliferated efficiently in culture. Independent of donor age, as few as 2 to 4 PAX7$^+$ satellite cells gave rise to several thousand myoblasts. Transplantation of human muscle fiber fragments into irradiated muscle of immunodeficient mice resulted in robust engraftment, muscle regeneration, and proper homing of human PAX7$^-$ satellite cells to the stem cell niche. Further, the inventors determined that subjecting the human muscle fiber fragments to hypothermic treatment successfully enriches the cultures for PAX7$^+$ cells and improves the efficacy of the transplantation and muscle regeneration. Finally, the inventors successfully altered gene expression in cultured human PAX7$^+$ satellite cells with Sleeping Beauty transposon-mediated nonviral gene transfer, highlighting the potential of this system for use in gene therapy. Together, these results demonstrate the ability to culture and manipulate a rare population of human tissue-specific stem cells and suggest that these PAX7$^+$ satellite cells have potential to restore gene function in muscular dystrophies.

Introduction

Satellite cells are the proper stem cells of the adult skeletal muscle. Like other stem cell types, these cells are maintained over very long time periods (1, 2). Despite their characterization as early as 1961, satellite cells have only been recognized recently as indispensable for muscle regeneration (3-5). Satellite cells are notoriously difficult to study due to their low abundance and their dispersed location in the specific stem cell niche, the space between basal lamina and sarcolemma of skeletal muscle. Recent animal experiments have allowed deeper insight into the function and regulation of satellite cells (2, 6-9). The studies indicated that satellite cells have an enormous potential for self-renewal and superb potential for muscle regeneration. However, expansion of human satellite cells for therapeutic purposes has not been successful. Therefore, therapy-oriented research has favored the use of other cell populations with myogenic potential, such as CD133$^+$ cells, pericytes, inducible stem cells, mesoangioblasts, or PW1 cells (10-14). These cells are abundant, more accessible, and transverse blood vessels.

However, compared with satellite cells, such alternative cell types have limited ability to form muscle stem cells (satellite cells) and to regenerate muscle tissue. Satellite cells appear during development, and their differentiation and survival depends on the paired box proteins PAX3 and PAX7 (2). While PAX3 plays a key role in embryonic satellite cell development, PAX7 predominantly directs their postnatal survival (15, 16). PAX7 is expressed postnatally and is a reliable satellite cell marker (17). Additional markers like CD56 (NCAM), CD34, CXCR4, m-cadherin, α7-integrin, MET, syndecan-3, and syndecan-4 characterize murine muscle satellite cells (18-22), but their relevance for the identification of human satellite cells has not been established. After skeletal muscle injury, quiescent satellite cells become activated and either self renew or enter a differentiation program that culminates in fusion to the syncytial muscle fiber. Several factors and pathways drive this complex cascade, including myogenic regulatory factors (such as MYF5, MYOD, and myogenin) and signaling systems (such as WNT and NOTCH) as well as yet ill-defined factors provided by the extracellular matrix or systemic sources (reviewed in ref. 23).

Early transplantation studies demonstrated a promising contribution of mouse myoblasts to regeneration of host fibers in the mdx mouse model of Duchenne's muscular dystrophy (24). Shortly thereafter, clinical trials were conducted and were based on the injections of cultured postnatal human myoblasts into muscle of patients with Duchenne's muscular dystrophy. Unfortunately, transplanted myoblasts showed poor survival, low ability to migrate, and made little contribution to fiber regeneration (25-27). The aim of aspects of the invention was to develop tools to render human muscle stem cells manageable for research on muscle regeneration and for gene therapy in muscular dystrophies and other muscle-wasting disorders.

Results

PAX7$^+$ Satellite Cells on Freshly Isolated Human Muscle Fiber Fragments

The inventors obtained 69 different specimens of fresh muscle tissue from adult human subjects (age 20-80 years, 34 female and 35 male donors) after due approval and written, informed consent. Human muscle fiber fragments (HMFFs) were dissected manually, without enzymatic treatment (cf. FIG. 1 and Supplemental FIG. 1 of the publication). The inventors isolated and analyzed 884 fragments containing 1-8 fibers, as indicated in the following Table 1.

TABLE 1

Summary of experiments

| Number of muscle biopsy specimens | Age and gender of donors | Procedure | Number of experiments |
|---|---|---|---|
| 69 | 20-80 years 34 male, 35 female | HMFF characterization | 580 HMFF |
| | | Characterization of colonies that grew onto culture dish | 304 HMFF |
| | | Characterization of colonies after hypothermic treatment (4° C.) | 272 HMFF |
| 6 | 44-64 years 3 male, 3 female | Transplantation | 33 transplantations in TA muscle |

The inventors used various antigens previously characterized in mice to identify human satellite cells in freshly isolated HMFFs. Coimmunostaining for PAX7 and the neural cell adhesion molecule NCAM (CD56) (cf. FIG. 1B of the publication) reliably identified cells associated with the human fibers. The majority (80%) of these were double positive for PAX7 and NCAM, but similar proportions of cells staining were also observed either only for PAX7 or only for NCAM. Rarely, MYF5$^+$/PAX7$^+$ cells were found (cf. FIG. 1B of the publication). 2% to 4% of all nuclei in skeletal muscle fibers were PAX7$^+$. The inventors noted no major differences in the proportion of PAX7$^+$ nuclei associated with fibers in different age groups.

The inventors also tested other markers, such as MET, CXCR4, and CD34. MET$^+$ cells were abundant in a skeletal muscle biopsy specimen obtained from a 3-month-old child but were not present on muscle sections from adult donors. Occasionally, the inventors identified CD34$^+$ or CXCR4$^+$ cells in adult muscle specimens or muscle fiber preparations, but these did not costain for PAX7 and were not located in the satellite cell niche. Therefore, these markers were not used further to identify satellite cells in humans (cf. Supplemental FIG. 2 of the publication). Subsequently, it will be referred to PAX7$^+$ cells as human satellite cells.

Culture of HMFFs

Next, it was tested whether satellite cells in HMFFs are viable and can be cultured. In cultured HMFFs, cells remained motile for up to 10 days (cf. Supplemental Video 1 of the publication). During the first days of culture, satellite cells remained associated with the fiber and did not grow out on the culture dish. Instead, they associated with the remaining scaffold of the fiber fragment and located inside the fiber, in which they were densely packed. After 5 to 10 days, the cells moved out of the fiber onto the culture dish and formed the first colonies.

During the time that PAX7$^+$ cells remained associated with cultured fibers (5-10 days), their number increased considerably, and the inventors estimated a 20- to 50-fold increase in quantity compared with that of freshly prepared fragments (cf. FIG. 2A of the publication). The majority of such cells were desmin$^+$, and many were MYF5$^+$/desmin$^+$ (cf. FIGS. 2A and 2B of the publication), indicating that they correspond to activated satellite cells. Activation of satellite cells, as assessed by the appearance of large groups of PAX7$^+$ and desmin$^+$ cells, was observed in 100% of the cultured HMFFs, independent of the age of the donors. After 3 weeks of culture, the numbers of PAX7$^+$ (but not desmin$^+$) cells associated with the HMFFs declined, indicating that the myogenic cells began to differentiate (cf. FIG. 2A of the publication). The basal lamina provided an outer shell for the HMFFs in culture (cf. FIG. 2C of the publication).

The inventors also analyzed cells that no longer associated with the fiber and had formed a colony on the culture dish (cf. FIG. 3A, top row, of the publication). In 2-week-old HMFF cultures, the number of such cells was always high, and colonies containing around 1,000 to 2,000 cells were observed.

The cells in these colonies were heterogeneous, i.e., usually most were desmin$^+$. Some had fused into myotubes, and the proportion of PAX7$^+$ cells was variable (10%-50%), even when the HMFFs were obtained from the same donor (cf. FIG. 3A, middle row, of the publication). BrdU pulse labeling (22 hours) confirmed that many cells (50%) in the colonies were proliferating (cf. FIG. 3A, bottom row, of the publication). The fraction of nonmuscle cells (desmin$^-$ cells) in the colonies varied between 5% and 25% and, on rare occasions, was as high as 70%. However, the proportion was not higher in HMFF cultures from aged donors.

Growth factors and substrate rigidity are important for satellite cell maintenance and proliferation (28). Matrigel contains a mixture of matrix proteins and growth factors, and Matrigel-coated substrates are used frequently for cultures of mouse myogenic cells. The inventors compared HMFFs cultured on culture plastic with or without Matrigel for 7 to 14 days and observed neither obvious differences in the formation of colonies outside the fiber nor changes in the colony size (cf. Supplemental FIG. 3 of the publication). Thus, the scaffold provided by the fibers themselves suffices to stimulate initial activation and proliferation of satellite cells, independent of external factors provided by Matrigel. Culture conditions without additives like Matrigel will be particularly suited in experiments with cells used for retransplantations into patients.

Sleeping Beauty-Based Gene Transfer Can Be Applied to HMFF-Satellite Cells

It was then tested whether gene delivery can be achieved in satellite cells in cultured HMFFs. Muscle fiber fragments were cultured for 2 days and then cotransfected with a Sleeping Beauty transposon-based vector encoding the fluorescent protein Venus (pT2-CAGGS-Venus) and a second expression plasmid encoding the CMV-SB100X transposase. Venus$^+$ satellite cells were visible 1 day after transfection. After these cells had moved onto the culture dish, Venus$^+$ myoblasts were present for up to 35 days (cf. FIG. 3B of the publication).

Satellite Cells From HMFFs Contribute to Muscle Regeneration After Engraftment Into Mice.

Next, HMFFs were transplanted into anterior tibialis muscles of NOG mice (n=33). For transplantation, HMFFs cultured for 5 to 7 days were used, i.e., fibers containing activated satellite cells that had not yet left the fiber. HMFFs from biopsy specimens obtained from 6 donors (aged 44-64 years) were transplanted, as indicated in the following Table 2 (experimental groups A-D).

TABLE 2

Transplantation of HMFFs into NOG mice

| Group | Donor[A] | Pre-treatment of HMFFs | Successful transplantations[B] | Irradiation (Gy) | Human cells after 3 weeks[C] | Human cells after 7 to 8 weeks[C] | Multinuclear human fibers, PAX7+ cells |
|---|---|---|---|---|---|---|---|
| A | 44 f, 47 f | No | 9/10 | No | 5-150 | 5-150 | No |
| B | 53 m | No | 1/3 | 9 | 5-50 | n.t. | No |
| C | 53 m, 64 f | No | 8/10 | 18 | 5-300 | 5-300 | Few |
| D | 62 m, 64 m | ht for 3 weeks | 6/10 | 18 | 5-150 | n.t. | Frequent |

[A]Age in years and gender;
[B]transplants with human cells per total number of transplanted tibialis anterior muscles;
[C]number of human nuclei per cryosection.
f, female;
m, male;
n.t., not tested;
ht, hypothermic treatment.

When fibers were transplanted into nonirradiated muscle or into muscle irradiated with 9 Gy, few human nuclei were present 3 or 8 weeks after the transplantation, as assessed by the presence of human lamin A/C detected by an anti-human-specific lamin A/C antibody. Almost all human lamin A/C+ nuclei were located in the interstitium and not integrated in the muscle fibers (cf. FIG. 4 of the publication). After focal irradiation of the muscle with 18 Gy, engraftment of human myoblasts was readily observed 3 or 7 weeks after transplantation (cf. FIG. 4 of the publication). At the earlier time point, myotubes and myofibers containing human nuclei were detectable, but human nuclei were more abundant in muscle fibers 7 weeks after transplantation. Occasionally, murine and human nuclei were present in hybrid myofibers (cf. FIG. 5B of the publication). The size of the largest dissemination of human nuclei was 800×400×400 μm.

Hypothermic Treatment of HMFFs Enriched Cultures for Myogenic Cells and Improved Transplantation Efficacy Next, it was tested whether HMFFs used as a source for satellite cells are storable, which would be advantageous for autologous transplantation and gene repair experiments. Glucose-containing buffered salt solution (Solution A) did not permit survival of muscle stem cells. However, when HMFFs were kept at 4° C. in medium with low serum (OptiMEM) (hypothermic treatment) without oxygenation for as long as 35 days and subsequently cultured them at 37° C. and 21% oxygen (cf. experimental design III in FIG. 1A and FIG. 3C of the publication), satellite cell colonies outgrowing the fiber were detected. Hypothermic treatment resulted in delayed formation of colonies on the culture dishes, i.e., the first colonies were observed after 2 weeks, and some colonies appeared only after 6 weeks of HMFF culture. Remarkably, colonies from HMFFs subjected to hypothermic treatment contained 100% myogenic cells (desmin+ cells) (cf. FIG. 3D of the publication). Thus, nonmyogenic cells like fibroblasts did not survive prolonged storage at hypothermic conditions. Although the colonies only consisted of myogenic cells, they were heterogeneous, containing PAX7+ cells (between 20% and 60%), cells that express MYF5 and MYOD, and frequently fusing myotubes (cf. FIG. 3D of the publication). After BrdU labeling, colonies from HMFFs subjected to hypothermic treatment and freshly obtained HMFFs displayed similar labeling indices.

Freshly isolated HMFFs always gave rise to colonies, but, after hypothermic treatment, outgrowth was more variable and myoblasts grew only from 50% of HMFFs. Colony formation after hypothermia and hypoxia did not correlate with donor age. Hypoxia is known to activate NOTCH signaling, and NOTCH is known to be important for satellite cell maintenance (29-31). The presence of DAPT, a γ-secretase and NOTCH signaling inhibitor, during hypothermic treatment did not interfere with survival of satellite cells, and similar colony sizes and numbers of PAX7+ cells in HMFF cultures were observed regardless of the presence or absence of the inhibitor during storage at 4° C. (cf. FIG. 3D of the publication).

It was then tested whether HMFFs after hypothermic/hypoxic treatment could be transplanted successfully. HMFFs were kept at 4° C. for 3 weeks, placed into 37° C. tissue culture for 2 weeks, and then transplanted into mouse tibialis anterior muscles. Analysis 3 weeks after transplantation revealed that the transplants had participated in muscle regeneration more efficiently than HMFFs without hypothermic treatment. Muscle fibers in the transplants contained more and multiple human nuclei (cf. FIG. 4 and FIG. 5A of the publication).

Further, human lamin A/C+ cells that coexpressed PAX7 were detected in a satellite cell position below the lamina (cf. FIG. 5B of the publication). A quarter of the human nuclei were PAX7+ in one section of one transplant. Only very few human nuclei were detected in the interstitium. Lack of nonmyogenic cells like fibroblasts might account for this difference.

Discussion

The inventors investigated a long-term tissue culture model to define properties and growth characteristics of human satellite cells that remained associated with muscle fibers (HMFF culture). A detailed characterization is provided, beginning with the quiescent satellite cell located in the stem cell niche, their subsequent activation, migration, and differentiation. It could be shown that enrichment and expansion of satellite cells is feasible, that cultured human fiber fragments can be transplanted and contribute to muscle regeneration, and that they generate human satellite cells that home correctly to the satellite cell niche. Further, using transposon-mediated gene insertion into the genome (Sleeping Beauty System), gene delivery was accomplished in satellite cells in cultured fibers.

Simple expansion of satellite cells in culture results in rapid differentiation, and the cell population with self-renewal and regenerative potential is rapidly lost (32). Others have used suspensions of cultured human primary satellite cells (myoblasts) in transplantation experiments; however, such transplanted cells survive poorly and do not contribute to fibers.

The inventors were able to show that cultured and transplanted HMFFs can fuse to muscle fibers and participate in the endogenous stem cell pool, indicating that fiber culture overcomes the previous limitations of cultured human primary satellite cells (myoblasts).

Recent work has provided important insight into satellite cell biology, revealing molecular mechanisms that might help to expand and maintain such stem cells. For instance, culture of murine satellite cells on soft hydrogel substrates rather than rigid plastic enriches cultures for a self-renewing stem cell population with improved regenerative efficacy (28). The HMFF culture system introduced here provides a 3-dimensional environment with a soft matrix and shows that satellite cells in vivo also use damaged fibers as scaffolds during regeneration.

In addition to satellite cells, HMFFs contain other cell types like fibroblasts. In accordance, colonies from freshly cultured HMFFs also contain nonmyogenic cells, but such nonmyogenic cells are no longer observed when HMFFs are stored for prolonged periods at 4° C. prior to culture. Quiescent stem cells survive under extreme conditions, for instance, in postmortem tissue (33) or under hypoxic microenvironments (reviewed in ref. 29). Metabolic requirements of quiescent satellite cells appear distinct from those of activated stem cells or from other cell types, such as fibroblasts. The long-term survival of satellite cells and their enrichment will be advantageous in cell replacement or gene therapy approaches, as they imply the option of storing the muscle fibers for several weeks.

The inventors found that gene transfer can be applied successfully to cultured satellite cells, which are associated with HMFFs. The inventors documented the delivery of a Venus cDNA gene using the Sleeping Beauty transposon system. Transposons can be considered to represent natural gene delivery vehicles. Tranposon-based tools are versatile and can be used in gene therapy (34, 35). SB100X-mediated gene transfer allows stable, long-term gene expression in various primary cells and stem cells and functions over a broad range of cDNA size. Thus, transposon-based gene transfer might be suitable for deliver transgenes that encode very large muscle proteins, such as the full-length dysferlin or dystrophin, into cells that are transplanted into skeletal muscle.

Local irradiation was a prerequisite for successful engraftment and for participation of transplanted cells in muscle regeneration. Endogenous stem cells in the healthy muscles of the recipients are damaged by this procedure, indicating that the transplanted cells only contribute to regeneration when endogenous stem cells are impaired. In contrast to other protocols, apart from a small muscle incisure, into which the HMFF fragments were deposited, no additional damage, like freeze trauma or cardiotoxin, was applied.

It is noteworthy that in the most efficient transplants observed, every fiber in the damaged and regenerating area contained a human nucleus. Restoration of 10% gene activity could be sufficient for therapy in muscular dystrophies, indicating that the participation of transplanted cells observed here might already be beneficial.

Human satellite cells are scarce and can currently not be isolated by FACS. Indeed, the low number of satellite cells in HMFFs would not allow sorting, even if a suitable surface marker was available. Cultured HMFFs containing satellite cells might provide starting material for autologous cell transplantation for treatment of muscular dystrophies, provided that efficient gene delivery can be achieved. The inventors observed that HMFFs obtained from all adult subjects analyzed here contained human satellite cells that could be expanded in culture. Autologous satellite cells provide an advance over nonautologous cell sources (for instance, satellite cells obtained from human cadavers, ref. 33), circumventing difficulties associated with obtaining tissue or the life-long requirement of immunosuppressant after allotransplantation.

Autologous transplantation of HMFFs after correction of the disease-causing mutation may not overcome all known disadvantages of myoblast transplants, such as lack of direct access to specific muscle groups (e.g., diaphragm) or lack of alternative delivery routes that are precluded by the inability of the delivered cells to migrate across vessels. Indeed, limited migration of human cells from the insertion site after muscle transplantations of HMFFs was observed. This state of affairs is similar to the restricted dispersal of transplanted cells described in previous experiments that used different sources of satellite cells/myoblasts and transplantation protocols. It is possible that local application of autologous human satellite cells combined with intravenous application of other cell types, such as $CD133^+$ cells that possess the capacity for transvessel migration, will provide a route to more efficient therapies of muscular dystrophies.

Methods

Patients and Materials

HMFFs were prepared from muscle specimens obtained during hip surgery from individuals without neuromuscular disorders or for diagnostic purposes (ethical approval EA1/203/08, Charite). In total, 1,156 fiber bundles from 69 subjects were analyzed. Donor age ranged from 20 to 80 years; 34 were men and 35 were women. Analysis of frozen sections included an additional biopsy specimen (3 months of age) taken for diagnostic purposes after permission.

Preparation of Single HMFF Cultures

Immediately after biopsy, the muscle specimen was transferred into Solution A, which contains 30 mM HEPES, 130 mM NaCl, 3 mM KCl, 10 mM d-glucose, and 3.2 µM Phenol red (pH 7.6). Dissection of single fiber fragments was performed mechanically using miniature forceps under a stereomicroscope (Leica Microsystems). Secondary bundles were dissected by cutting the perimysial fascia, followed by the dissection of primary bundles in the same way. Primary bundles were carefully loosened to obtain single fibers. Single fiber fragments of a length of 2 to 3 mm were further mechanically relieved of connective tissue. HMFFs were either placed on Matrigel-coated (BD Biosciences) coverslips or cultured in regular plastic dishes. HMFFs were cultured in Skeletal Muscle Growth Medium (SMGM, PromoCell) supplemented with 10% FCS, glutamax, and gentamicin and cultured in a humidified atmosphere containing 5% $CO_2$ at 37° C.

For characterization of fresh single fibers, isolated fiber fragments were fixed in 4% PBS-buffered formaldehyde immediately after mechanical dissection. Staining of freshly prepared muscle fibers was initiated within 45 minutes after the biopsy was taken. HMFF cultures were set up within 2 hours after the biopsy procedure or subjected to hypothermic treatment. In hypothermic treatment, muscle specimens were placed in Solution A or in serum-reduced optimized minimal essential medium (OptiMEM, Life Technologies) and deposited at 4° C. for up to 35 days. The stored muscle was not specifically aerated.

Sleeping Beauty-Based Gene Transfer to HMFFs

Gene delivery studies were performed using the hyperactive Sleeping Beauty transposase SB100X (32). Cotransfection of HMFFs with a Sleeping Beauty transposon-based vector encoding the fluorescent protein Venus (pT2-CAGGS-Venus) and an expression plasmid for CMV-SB100X transposase was performed 2 days after isolation in SMGM. 400 ng pT2-CAGGS-Venus vector and 20 ng SB100X were diluted in 75 µl jetPRIME buffer (Polyplus-transfection SA) mixed with 2 µl jetPRIME reagent (Polyplus-transfection SA), incubated for 15 minutes at room temperature, and added to fiber cultures. Twelve hours after transfection, the medium was replaced by fresh SMGM. Analyses were performed between 1 and 35 days after transfection.

Immunohistochemistry

For immunohistochemical staining, muscle cryosections (6 µm) were fixed in 3.7% formaldehyde. HMFFs and cultured myoblasts were permeabilized in 0.2% Triton X-100 for 10 minutes and incubated in 1% BSA/PBS for 45 minutes; frozen sections were incubated in 5% normal goat serum/PBS for 45 minutes. Primary antibodies were used as described in Supplemental Table 2 and incubated for 4 to 16 hours at 4° C. After washing, samples were incubated with secondary antibodies (Cy3-conjugated anti-rabbit, Cy3-conjugated anti-rat, Alexa Fluor 488-conjugated anti-mouse antibodies, each 1:1,000) and Hoechst 1(:1,000) for 45 minutes in 1% BSA/PBS at room temperature. Alternatively, UEA (1:100, Vector Labs) was used for staining of endothelial layers of capillaries. For PAX7 staining, muscle sections were incubated in preheated antigen-unmasking Vector buffer (80° C., Vector Labs) for 15 minutes, fixed in Zamboni fixative (PFA/picric acid, pH 7.3) for 20 minutes, and, after additional washing, incubated in blocking buffer (10% horse serum, 0.5% blocking reagent [PerkinElmer], 0.1% Triton X-100 in PBS). Subsequently, sections were incubated with anti-PAX7 hybridoma supernatant for 12 hours. Sections were washed in PBS/0.1% Triton X-100 and incubated with fluorescence-conjugated secondary antibodies for 30 minutes.

Samples were imaged with a Leica DMI 6000 (Leica Microsystems) or a Zeiss LSM 700 confocal microscope (Carl Zeiss Microimaging GmbH). Images were composed and edited in Photoshop CS (Adobe) or CorelDRAW X5. 3-dimensional visualization of z-stacks was performed with Amira (Visage Imaging). As a rule, all modifications were applied to the whole image. Time-lapse microscopy was performed with a Leica DMI 6000 in a humidified atmosphere at 37° C. and 5% CO2. All antibodies and dilutions are listed in the following Table 3.

TABLE 3

Antibodies used for immunohistochemistry

| Antibody | Species | Working concentration | Catalog number, Company |
| --- | --- | --- | --- |
| Anti-BrdU | rat | 10 µg/ml | ab 6326, Abcam, Cambridge, UK |
| Anti-CD34 | rabbit | 2 µg/ml | sc-9095, Santa Cruz Biotechnology, Santa Cruz, CA, USA |
| Anti-CXCR4 | rabbit | 2.5 µg/ml | ab 2074, Abcam |
| Anti-c-met | rabbit | 2 µg/ml | sc-161, Santa Cruz Biotechnology |
| Anti-desmin | mouse | 1:500 (cells) 1:50 (histology) | M 0760, Dako, Glostrup, Denmark |
| Anti-desmin | rabbit | 4 µg/ml | ab 8592, Abcam |
| Anti-hu Lamin A/C | rabbit | 1:2000 | ab 108595, Epitomics, Cambridge, UK |
| Anti-β2 laminin | mouse | 0.1 µg/ml | Novus Biologicals, Littleton, CO, USA |
| Anti-Myf5 | rabbit | 0.2 µg/ml | sc-302, Santa Cruz Biotechnology |
| Anti-MyoD | mouse | 1 µg/ml | sc-32758, Santa Cruz Biotechnology |
| Anti-NCAM (CD56) | mouse | 2 µg/ml | 130-090-955, Miltenyi Biotech, Bergisch Gladbach, Germany |
| Anti-Pax7 | mouse | Supernatant, undiluted | DSHB, Iowa City, Iowa, USA |

Focal Irradiation of Tibialis Anterior Muscle

Female 6-week-old NOD.Cg-Prkdc$^{scid}$ Il2rg$^{tm1Sug}$/JicTac mice (referred to as NOG mice herein) (Taconic) were anesthetized with ketamine-xylazine in PBS (9 mg/ml ketamine, 1.2 mg/ml xylazine) with a dose of 160 µl/20 g administered by intraperitoneal injection. To provide a reproducible position for the mice, an acrylic glass block with surface fiducial markers was constructed. For the calculation of digitally reconstructed radiographs (DRRs) as well as for treatment planning, a computed tomography (CT) scan, with 0.75-mm slice thickness, was conducted with a dedicated CT scanner (Siemens Emotion). This CT data set served as an exemplary basis for calculation of the DRRs, for tracking, and for radiation dose distribution, assuming all legs and muscles of the selected mice were similar. The CT volume data set was used for target delineation of the murine body as organ at risk. The prescription dose was 18 Gy, as earlier proposed by Boldrin et al. (36). Because of the inherent inhomogeneity of dose distribution, a maximum of 19.5 Gy was accepted in the targeted leg, with the 90% isodose line completely enclosing the target region.

All mice were treated with a single irradiation fraction of 18 Gy using the image-guided robotic system (CyberKnife Radiosurgery System, Accuray Inc.) (cf. Supplemental FIG. 4 of the publication). The mice were placed in the customized acrylic mold with attached fiducial markers. The fiducial markers were used for superimposing the live positioning images during the treatment procedure with previously calculated radiograms. The 3-dimensional correction values were used by the robotic treatment couch. The treatment procedure itself could be conducted within a 5-minute time span.

Transplantation of HMFFs Into Murine Tibialis Anterior Muscle

Mice were placed under anesthesia using ketamine-xylazine (9 mg/ml ketamine, 1.2 mg/ml xylazine) with a dose of 160 µl/20 g. Anterior tibial muscles were cut longitudinally, and HMFFs (4-8 muscle fibers) were placed inside the muscle parallel to the orientation of the murine fibers. The tibialis anterior muscles were closed without sutures. The overlying skin was closed using polyglycolic acid threads (MARLIN violett HR22, USP 4/0, EP 1.5 threads; Catgut GmbH). For assessment of the transplants, tibialis anterior muscle was cut horizontally in the middle, and every tenth section into the upper and lower part of the muscle was stained for human lamin A/C and desmin.

Study Approval

The internal review board of Charité approved the study, and written, informed consent was obtained from all participants (EA1/203/08 and EA2/041/10). Animal studies were performed under license G0016/13.

LIST OF REFERENCES CITED IN THE PRECEDING SECTIONS

1. Mauro A. Satellite cell of skeletal muscle fibers. *J Biophys Biochem Cytol.* 1961; 9(2):493-495.
2. Relaix F, Rocancourt D, Mansouri A, Bucking-ham M. A Pax3/Pax7-dependent population of skeletal muscle progenitor cells. *Nature.* 2005; 435(7044):948-953.
3. Lepper C, Partridge T A, Fan C M. An absolute requirement for Pax7-positive satellite cells in acute injury-induced skeletal muscle regeneration. *Development.* 2011; 138(17):3639-3646.
4. Sambasivan R, et al. Pax7-expressing satellite cells are indispensable for adult skeletal muscle regeneration. *Development.* 2011; 138(17):3647-3656.
5. Relaix F, Zammit P S. Satellite cells are essential for skeletal muscle regeneration: the cell on the edge returns centre stage. *Development.* 2012; 139(16):2845-2856.
6. Vasyutina E, Lenhard D C, Wende H, Erdmann B, Epstein J A, Birchmeier C. RBP-J (Rbpsuh) is essential to maintain muscle progenitor cells and to generate satellite cells. *Proc Natl Acad Sci USA.* 2007; 104(11):4443-4448.
7. Bröhl D, et al. Colonization of the satellite cell niche by skeletal muscle progenitor cells depends on Notch signals. *Dev Cell.* 2012; 23(3):469-481.
8. Rocheteau P, Gayraud-Morel B, Siegl-Cachedenier I, Blasco M A, Tajbakhsh S. A subpopulation of adult skeletal muscle stem cells retains all template DNA strands after cell division. *Cell.* 2012; 148(1-2):112-125.
9. Conboy I M, Rando T A. The regulation of Notch signaling controls satellite cell activation and cell fate determination in postnatal myogenesis. *Dev Cell.* 2002; 3(3):397-409.
10. Sampaolesi M, et al. Cell therapy of alpha-sarcoglycan null dystrophic mice through intra-arterial delivery of mesoangioblasts. *Science.* 2003; 301(5632):487-492.
11. Torrente Y, et al. Human circulating AC133(+) stem cells restore dystrophin expression and ameliorate function in dystrophic skeletal muscle. *J Clin Invest.* 2004; 114(2): 182-195.
12. Dellavalle A, et al. Pericytes of human skeletal muscle are myogenic precursors distinct from satellite cells. *Nat Cell Biol.* 2007; 9(3):255-267.
13. Mitchell K J, et al. Identification and characterization of a non-satellite cell muscle resident progenitor during postnatal development. *Nat Cell Biol.* 2010; 12(3):257-266.
14. Filareto A, et al. An ex vivo gene therapy approach to treat muscular dystrophy using inducible pluripotent stem cells. *Nat Commun.* 2013; 4:1549.
15. Relaix F, et al. Pax3 and Pax7 have distinct and overlapping functions in adult muscle progenitor cells. *J Cell Biol.* 2006; 172(1):91-102.
16. Oustanina S, Hause G, Braun T. Pax7 directs postnatal renewal and propagation of myogenic satellite cells but not their specification. *EMBO J.* 2004; 23(16):3430-3439.
17. Seale P, Sabourin L A, Girgis-Gabardo A, Mansouri A, Gruss P, Rudnicki M A. Pax7 is required for the specification of myogenic satellite cells. *Cell.* 2000; 102(6):777-786.
18. Beauchamp J R, et al. Expression of CD34 and Myf5 defines the majority of quiescent adult skeletal muscle satellite cells. *J Cell Biol.* 2000; 151(6):1221-1234.
19. Blanco-Bose W E, Yao C C, Kramer R H, Blau H M. Purification of mouse primary myoblasts based on α7 integrin expression. *Exp Cell Res.* 2001; 265(2):212-220.
20. Cerletti M, et al. Highly efficient, functional engraftment of skeletal muscle stem cells in dystrophic muscles. *Cell.* 2008; 134(1):37-47.
21. Cornelison D D, Filla M S, Stanley H M, Rapraeger A C, Olwin B B. Syndecan-3 and syndecan-4 specifically mark skeletal muscle satellite cells and are implicated in satellite cell maintenance and muscle regeneration. *Dev Biol.* 2001; 239(1):79-94.
22. Irintchev A, Zeschnigk M, Starzinski-Powitz A, Wernig A. Expression pattern of M-cadherin in normal, denervated, and regenerating mouse muscles. *Dev Dyn.* 1994; 199(4):326-337.
23. Yin H, Price F, Rudnicki M A. Satellite cells and the muscle stem cell niche. *Physiol Rev.* 2013; 93(1):23-67.
24. Partridge T A, Morgan J E, Coulton G R, Hoffman E P, Kunkel L M. Conversion of mdx myofibres from dystrophin-negative to -positive by injection of normal myoblasts. *Nature.* 1989; 337(6203):176-179.
25. Mendell J R, et al. Myoblast transfer in the treatment of Duchenne's muscular dystrophy. *N Engl J Med.* 1995; 333(13):832-838.
26. Gussoni E, et al. Dystrophin expression in the mdx mouse restored by stem cell transplantation. *Nature.* 1999; 401(6751):390-394.
27. Tedesco F S, Dellavalle A, Diaz-Manera J, Messina G, Cossu G. Repairing skeletal muscle: regenerative potential of skeletal muscle stem cells. *J Clin Invest.* 2010; 120(1):11-19.
28. Gilbert P M, et al. Substrate elasticity regulates skeletal muscle stem cell self-renewal in culture. *Science.* 2010; 329(5995):1078-1081.
29. Simon M C, Keith B. The role of oxygen availability in embryonic development and stem cell function. *Nat Rev Mol Cell Biol.* 2008; 9(4):285-296.
30. Gustafsson M V, et al. Hypoxia requires notch signaling to maintain the undifferentiated cell state. *Dev Cell.* 2005; 9(5):617-628.
31. Liu W, et al. Hypoxia promotes satellite cell self-renewal and enhances the efficiency of myoblast transplantation. *Development.* 2012; 139(16):2857-2865.
32. Montarras D, et al. Direct isolation of satellite cells for skeletal muscle regeneration. *Science* 2005; 309(5743): 2064-2067.
33. Latil M, et al. Skeletal muscle stem cells adopt a dormant cell state post mortem and retain regenerative capacity. *Nat Commun.* 2012; 3:903.
34. Ammar I, Izsvák Z, Ivics Z. The Sleeping Beauty transposon toolbox. *Methods Mol Biol.* 2012; 859:229-240.
35. Mátés L, et al. Molecular evolution of a novel hyperactive Sleeping Beauty transposase enables robust stable gene transfer in vertebrates. *Nat Genet.* 2009; 41(6):753-761.
36. Boldrin L, Neal A, Zammit P S, Muntoni F, Morgan J E. Donor satellite cell engraftment is significantly augmented when the host niche is preserved and endogenous satellite cells are incapacitated. *Stem Cells.* 2012; 30(9): 1971-1984.

Exemplary Embodiment: HMFF Outgrowth After Hypothermic Treatment

Human muscle fiber fragments (HMFFs) have been cultivated for 7 days and 12 days at 4° C. in different media. For methodic details, reference is made to the preceding exemplary embodiments since the preparation and cultivation steps were carried out in the same way.

After 7 days of hypothermic treatment in OptiMEM, satellite cells were grown out of 83% of the HMFFs. This number reduces to 28% after an overall hypothermic treatment of 12 days in OptiMEM. If the hypothermic treatment is even further prolonged, the number of grown-off satellite cells tend to zero.

By this experiment, it could also be shown that after 7 days of hypothermic treatment in OptiMEM 88% of the examined cultures were free of non-myogenic cells (namely 21 of 24 HMFF cultures). Expressed in other words, cultivated satellite cells were highly enriched in these cultures. If the incubation time is decreased below 7 days, the relative amount of non-myogenic cells increases dramatically. If the incubation time is below 4 days, basically no enrichment of myogenic can be observed.

Thus, at least in case of satellite cells, it is advisable to perform the hypothermic treatment over a period of 5 days to 4 weeks (28 days), in particular over a period of 7 days to 4 weeks (28 days), in particular over a period of 7 days to 3 weeks (21 days), in particular over a period of 7 days to 2 weeks (14 days), in particular over a period of 5 days to 2 weeks (14 days), in particular over a period of 5 days to 1 week (7 days), in particular over a period of around or exactly 1 week (7 days).

The precedingly discussed experiments are summarized in the following Table 4.

TABLE 4

Satellite cell outgrowth from HMFFs after hypothermic treatment in OptiMEM.

|  | 7 days hypothermic treatment in OptiMEM | 12 days hypothermic treatment in OptiMEM |
|---|---|---|
| Donor no. | 1419 | 1424 |
|  | 1420 | 1425 |
|  | 1422 | 1426 |
|  | 1423 | 1430 |
| Satellite cell outgrowth from HMFFs | 83% (53/64) | 28% (18/64) |
| Cultures with pure myogenic cells | 88% (21/24 HMFF cultures) | not determined |

After 7 days of hypothermic treatment in SolA (see above for composition of this medium), satellite cells were grown out of 45% of the HMFFs, whereas in a comparative experiment with OptiMEM using the same donors, an outgrowth rate of 51% could be observed. All examined cultures were free of myogenic cells.

The precedingly discussed experiments are summarized in the following Table 5.

TABLE 5

Satellite cell outgrowth from HMFFs after hypothermic treatment in OptiMEM or SolA.

|  | 7 days hypothermic treatment in OptiMEM | 7 days hypothermic treatment in SolA |
|---|---|---|
| Donor no. | 1440 | 1440 |
|  | 1441 | 1441 |
|  | 1442 | 1442 |
| Satellite cell outgrowth from HMFFs | 51% (24/47) | 45% (21/47) |
| Cultures with pure myogenic cells | not determined | 100% (9/9 HMFF cultures) |

The invention claimed is:

1. A method for cultivating and enriching human muscle satellite cells in vitro, comprising the following steps:
   obtaining a human muscle biopsy specimen from a living subject;
   mechanically isolating, without enzymatic treatment, muscle fiber fragments from the biopsy specimen to provide isolated muscle fiber fragments wherein the isolated muscle fiber fragments have a length of 2 to 3 mm;
   incubating the isolated muscle fiber fragments at about 4° C. to about 8° C. for a period of 5 days to 7 days;
   immediately after incubation, culturing the isolated muscle fiber fragments at about 37° C. under conditions sufficient for satellite cells present in the isolated muscle fiber fragments to form cell colonies that outgrow from the muscle fiber fragments; and
   collecting the satellite cells from the cell colonies, wherein 70% to 100% of viable cells collected from the cell colonies are satellite cells.

2. The method of claim 1, wherein 85% to 100% of all viable cells collected from the cell colonies are satellite cells.

3. The method of claim 2, wherein up to 85% of the satellite cells collected from the cell colonies express Pax7.

4. The method of claim 1, wherein 100% of the cells collected from the cell colonies express desmin.

5. The method of claim 1, comprising incubating the isolated muscle fiber fragments at about 5° C.

6. The method of claim 1, comprising incubating the isolated muscle fiber fragments within 2 hours of obtaining the human muscle biopsy specimen.

7. The method of claim 1, comprising incubating the isolated muscle fiber fragments for a period of time of 7 days.

* * * * *